United States Patent
Kim et al.

(10) Patent No.: US 10,322,210 B2
(45) Date of Patent: Jun. 18, 2019

(54) PREPARATION METHOD OF CORE-SHELL STRUCTURED FIBROUS SCAFFOLDS

(71) Applicant: INDUSTRY-ACADEMIC COOPERATION FOUNDATION, DANKOOK UNIVERSITY, Yongin-si (KR)

(72) Inventors: Hae-Won Kim, Cheonan-si (KR); Roman Perez, Cheonan-si (KR)

(73) Assignee: INDUSTRY-ACADEMIC COOPERATION FOUNDATION, DANKOOK UNIVERSITY, Yongin-si (KR)

( * ) Notice: Subject to any disclaimer, the term of this patent is extended or adjusted under 35 U.S.C. 154(b) by 13 days.

(21) Appl. No.: 14/037,174

(22) Filed: Sep. 25, 2013

(65) Prior Publication Data

US 2014/0186413 A1 Jul. 3, 2014

(30) Foreign Application Priority Data

Dec. 27, 2012 (KR) .................. 10-2012-0155310

(51) Int. Cl.
*A61L 27/46* (2006.01)
*A61L 27/54* (2006.01)

(52) U.S. Cl.
CPC ............... *A61L 27/46* (2013.01); *A61L 27/54* (2013.01); *A61L 2300/41* (2013.01); *A61L 2300/414* (2013.01); *A61L 2300/416* (2013.01)

(58) Field of Classification Search
None
See application file for complete search history.

(56) References Cited

U.S. PATENT DOCUMENTS

| | | | | |
|---|---|---|---|---|
| 5,800,829 A | * | 9/1998 | Dionne et al. ............... | 424/422 |
| 2006/0233851 A1 | * | 10/2006 | Simon .................. | A61L 27/427 |
| | | | | 424/422 |
| 2010/0068243 A1 | * | 3/2010 | Khairoun et al. ............ | 424/426 |
| 2010/0143439 A1 | * | 6/2010 | Jayasuriya .......... | A61L 27/3604 |
| | | | | 424/423 |

OTHER PUBLICATIONS

Perez et al., "Core-shell designed scaffolds of alginatelalpha-tricalcium phosphate for the loading and delivery of biological proteins," J. Biomed. Mater. Res. Part A: 00A:000-000, Sep. 26, 2012, 10 pages.
Lee et al., "Alginate combined calcium phosphate cements: mechanical properties and in vitro rat bone marrow stromal cell responses," *J Mater Sci: Mater Med* 22:1257-1268, 2011.
Notice of Preliminary Rejection, dated Sep. 20, 2016, for Korean Application No. 10-2012-0155310, 7 pages (with English Translation).

* cited by examiner

*Primary Examiner* — Johann R Richter
*Assistant Examiner* — Danielle Sullivan
(74) *Attorney, Agent, or Firm* — Seed IP Law Group LLP

(57) ABSTRACT

The present invention relates to a preparation method for core-shell structured fibrous scaffolds, and more specifically to preparing a core part composition and a shell part composition that each have different constitutions by adding calcium phosphate cement and a protein, drug of combination thereof to alginate solution, and then inserting the above core part composition and shell part composition to internal and external nozzle of concentric nozzle respectively to inject into calcium ion aqueous solution and thereby hardening them, thus preparing core-shell structured rapidly setting Alg/α-TCP scaffolds capable of controllably releasing a protein or drug.

8 Claims, 13 Drawing Sheets

PREPARATION METHOD OF CORE-SHELL STRUCTURED FIBROUS SCAFFOLDS

TECHNICAL FIELD

The present invention relates to a preparation method for core-shell structured fibrous scaffolds, more specifically, to a preparation method for core-shell structured rapidly setting Alg/α-TCP scaffolds that can controllably release a protein or drug. This is done by preparing a core part composition and shell part composition that have different constitutions through adding a calcium phosphate cement and a protein, a drug or a combination thereof to an alginate solution. The above core part composition and shell part composition is then inserted to the inner and outer nozzle of the concentric nozzle, respectively, in order to then be injected to a calcium ion solution intended to be hardened.

BACKGROUND ART

Designing scaffolds with a capacity to load and deliver therapeutic molecules such as growth factors enhances tissue regeneration. Many strategies have been developed for this purpose, which involve the adsorption/binding of growth factors on the surface or their incorporation within the scaffolds. (Ziegler J et al., *J Biomed Mater Rev,* 2002, 59, 422-428; King W J et al., *Adv Drug Deliv Rev,* 2012, 64, 1239-1256; Yun Y R et at., *J Tissue Eng.* 2010, 1, 218142; Wenk E et al., *Biomaterials,* 2009, 30, 2571-2581).

Generally, the growth factors adsorbed on the surface present substantial initial burst effects owing to the weak electrostatic interactions. On the other hand, when the growth factors were incorporated within the scaffold's micro/nanostmcture, they could be better secured and undergo more sustained release. Scaffolding conditions, including pH, solvent type, temperature, and ionic strength are factors in the incorporation of growth factors. (Fransson J et al., *I. Pharm Res,* 1997, 14, 606-612; van de Weert M et. al., *Pharm Res,* 2000, 17, 1159-1167).

Possible scaffold design strategies that have been researched include securing growth factors within capsules/particles that are subsequently incorporated within scaffolds, covering or layering scaffolds to protect the incorporated growth factor, use of water-soluble compositions, and self-hardening/setting. (Whitaker M J et al., *J Pharm Pharmacol,* 2001, 53, 1427-1437; Mourino V et al., *J R Soc Interface,* 2010, 7, 209-227; Sokolsky-Papkov M et al., *Adv Drug Deliv Rev,* 2007, 59, 187-206).

Along with the issue of loading growth factors within scaffolds, the method of delivery is of special importance in achieving optimal biological functions. One promising strategy is the delivery of dual/multiple growth factors in a timely and sequential manner. One example is the effects of combined growth factors incorporated within scaffolds on bone formation, which produces an initial release of angiogenic growth factors including vascular endothelial growth factors (VEGFs) followed by the sequential release of osteogenic factors, such as bone morphoqenetic proteins (BMPs), which act to synergize bone formation through the scaffolds. (Kempen D H R et al., *Biomaterials,* 2009, 30, 2816-2825). Strategic methods to develop scaffolds with dual/multiple growth factor delivery potential have been recently proposed. (Patel Z S et al., *Bone,* 2008, 43, 931-940; Shah N J et al., *Biomaterials,* 2011, 32, 6183-6193; Young S et al., *Tissue Eng A,* 2009, 15, 2347-2362).

Under these circumstances, the inventors of the present invention added a calcium phosphate cement and a protein, drug or a combination thereof to an alginate solution in order to a prepare a core part composition and shell part composition each having different constitutions, and afterward inserted the above core part composition and shell part composition into the inner and outer nozzle of the concentric nozzle, respectively, subsequently injecting them into a calcium ion aqueous solution. Afterward, the above core part composition and shell part, composition were hardened, confirming that rapidly setting Alg/α-TCP scaffolds having core-shell structures that, are capable of controllably releasing a protein or drug can be prepared through this process, thereby completing the present invention.

DISCLOSURE

Technical Problem

The objective of the present invention is to provide a preparation method for core-shell structured fibrous scaffolds capable of controllably releasing a protein or drug.

Another objective of this invention is to prepare core-shell structured fibrous scaffolds capable of controllably releasing a protein or drug.

Technical Solution

In order to achieve the above objective, the present invention provides a method for preparation of core-shell structured fibrous scaffolds comprising the following steps:

1) preparing a core part composition by adding calcium phosphate cement; and a protein, drug or combination thereof to an alginate solution (step 1);

2) preparing a shell part composition by adding calcium phosphate cement; and a protein, drug or combination thereof to an alginate solution (step 2); and 3) hardening the above core part composition and shell part composition by injecting the above core part composition and shell part composition to the calcium ion aqueous solution by way of inserting the above core part composition and shell part composition into the inner and outer nozzle of the concentric nozzle, respectively (step 3).

The present invention is characterized in that the above core part composition and shell part, composition have different constitutions.

The configuration of the present invention will be described in detail below.

The term "scaffold" of the present invention refers to a structure that provides a viable environment for proliferation and differentiation of cells which move from neighboring tissue as well as the adhesion and differentiation of cells which are disseminated into internal and external parts of the structure, and is one of the important basic factors in the tissue regeneration engineering field.

The above step 1, is a step of preparing the core part composition by adding calcium phosphate cement; a protein, drug or combination thereof to the alginate solution, which involves a step wherein the core part composition which forms the core part of fibrous scaffolds is prepared by adding calcium phosphate cement; a protein, drug or combination thereof to the alginate solution The term "alginate solution" in the present invention refers to a solution obtained by dissolving alginate in water.

The term "alginate" in the present invention refers to a metal salt of alginic acid. More specifically, sodium alginate or calcium alginate can be examples.

The above alginate solution of the present invention preferably has a concentration of 1 to 10 weight %, or more preferably, 3 to 5 weight %.

The term "cement" refers to hardened paste obtained through mixture of a powder in a solid state and liquid state. The "hardening" of above cement refers to a natural setting of the paste without artificial treatment at room temperature or body temperature. The paste herein refers to a result from mixture of the powder in a solid state and liquid state.

The term "calcium phosphate cement" in this invention refers to a cement in which powder in a solid state constitutes a mixture of calcium phosphate compound or calcium and/or phosphate compound.

The above calcium phosphate cement (CPC) is a material which consists of an aqueous solution containing powder of which the main component is calcium phosphate particles, and a substance which catalyzes hardening of the cement, such as a phosphate. When the two ingredients are mixed and applied in high viscosity liquid state, the calcium phosphate compound is precipitated and hardened by the chemical reaction of the two ingredients at the point where the above two ingredients are applied. During treatment, if the two ingredients are mixed and applied in high viscosity liquid state, the calcium phosphate compound is precipitated and hardened by the chemical reaction of two ingredients at the point where the above two ingredients are applied, and can be used for filling in empty space between damaged bones and healthy bones or bones and implants thereby fixing and stabilizing the two, acting as a bone substitute.

In the present invention, it is preferable that the amount or said calcium phosphate cement is 10 to 75 weight % among total core part composition.

In the present invention, the above calcium phosphate may be tricalcium phosphate, monocaicium phosphate, tetracalcium phosphate, ciicalcium phosphate, hydroxyl apatite or a combination thereof, but is not limited thereto.

In one example of the present invention, storage modulus (E') and loss modulus (E") values became higher as the added amount of α-TCP increased, when alginate was used with α-tricalcium phosphate (α-TCP) as opposed to when alginate alone was used, thereby confirming the superior-technical features of the present invention. Therefore, it has been confirmed that use of an alginate solution having α-TCP added is more preferable. (Example 2, FIG. 2).

Also, in another example of the present, invention, the addition of α-TCP to either the core part or shell part increased both storage modulus (E') and loss modulus (E") values. Overall, it could be observed that elasticity was higher as the amount of total α-TCP existing in the core part and shell part increased. Therefore, it could be confirmed that it is preferable to add α-TCP to alginate solution in usage. (Example 5, FIG. 8).

Also in another example of the present invention it was demonstrated that, compared to when alginate alone was used, usage of α-tricalcium phosphate (α-TCP) with alginate makes preparation of scaffolds that show a continuous and sustainable release profile of cytochrome C feasible, disregarding the crosslinking time (Example 4, FIG. 6). Therefore, it has been confirmed that α-TCP/Alg composite scaffolds are potentially useful for continuous long-terra delivery of a protein or drug.

In the present invention, the above protein can be growth factor, bovine serum albumin, lysozyme or combination thereof, but is not limited thereto. Specifically the above growth factor can be bone formation factor, angiogenesis factor of combination thereof, but is not limited thereto.

In the present invention, the above drug can be antibiotics, an anticancer drug, anti-inflammatory drug or a combination thereof, but is not limited thereto.

The above step 2 relates to the preparation of a shell part composition by adding calcium phosphate cement; and a protein, drug or combination thereof to an alginate solution which involves a step of preparing the shell part composition that forms the shell part of fibrous scaffolds by adding calcium phosphate cement; and protein, drug or combination thereof to alginate solution.

In the present invention, the types, concentration, amount of alginate solution, calcium phosphate cement, protein, and drug are identical to those detailed in the disclosure of the above core part composition.

The above step 3 relates to setting the above core part composition and shell part composition by inserting them into the inner and outer nozzle of the concentric nozzle, respectively, and subsequently injecting the core part composition and shell part composition into a calcium ion aqueous solution. Step 3 involves inducing self-setting of the core part composition and shell part composition by injecting them into the calcium ion aqueous solution through insertion into the inner and outer nozzle of the concentric nozzle.

In the present invention, it is preferable for the concentration of the above calcium ions to be 10 mM to 3 M. If the concentration of the calcium ions is lower than the lower bound, it might be difficult for hardening to take place. When concentration of the calcium ions is higher than the upper bound, there is risk of form alteration due to sudden hardening.

In the present invention, it is preferable that the hardening time of the above step 3 is 1 to 10 minutes. If the hardening time is less than the said lower bound, there is a disadvantage of the hardening process not being fully completed. If the hardening time is longer than the said upper bound, there is a disadvantage of an increase in the release of protein or drug loaded within the scaffolds.

The present invention can prepare fibrous scaffolds of a core-shell structure that has various release profiles by altering the composition of the above core and shell part.

Specifically, scaffolds with preferable release profile can be provided by altering the composition of the core part and shell part through placing the protein or drug that, requires fast release in the shell part, and placing the protein or drug that requires slow release in the core part.

In one Example of the present invention, release behavior was observed after loading cyt C to any one of the core part or shell part, by using Alg core-shell scaffolds. The results showed that cyt C that, was released from the core part, showed a more delayed release profile compared to cyt C that, was released from the shell part. Therefore, it was confirmed that the release profile of protein or drug can be controlled by changing the loading location of the protein or drug. (Example 5, FIG. 9a).

Also, by altering differently the α-TCP content in the core part composition or shell part composition, the release speed of scaffolds can be controlled.

In one Example of the present invention, observation of long-term release behavior of scaffolds obtained by changing the amount of α-TCP showed that the total amount of release for 10, 50, and 75 weight % α-TCP was ~35, ~48, and ~80% after 6 weeks, respectively, confirming that that total amount of release increased along with the increase of the amount of α-TCP. Therefore, it was confirmed that that release speed of scaffolds can be controlled by controlling the change in α-TCP amount (Example 4, FIG. 6).

Also, in one other Example of the present invention, observation of release of cyt C was made after the composition in either the core part or shell part was changed, while also changing the amount of α-TCP. As a result, when cyt C was loaded into the shell part, the shell part structure showed lower initial burst and on-going release profile, similar to what was observed in the above single fibrous scaffolds (FIG. 6) (Example 5, FIG. 9b).

Also, when cyt C is loaded into the core part, changing the composition of any one of shell part or core part was shown to affect the release of the protein (FIG. 9c). Specifically, when the composition of the core part was pure Alg, release of cyt C from the core part changed only slightly, depending on the composition of the shell part (FIG. 9c, green line (-▲-) and blue line (-♦-)). However, it was confirmed that cyt C release from the core part was substantially increased when the composition of the core part was 50% α-TCP/Alg, compared to when the composition of the core part, was Alg alone (FIG. 9c, red line (-■-) and purple line (-×-)). Also, the above release was significantly higher when the composition of the core part was 50% α-TCP/Alg, compared to when the shell part comprised 10% α-TCP (FIG. 9c, purple line (-×-) vs red line (-■-)). Particularly, it was confirmed that total release of cyt C was as high as 80 to 100% on day 42, and continuous release occurs after day 5 (FIG. 9c, red line (-■-).

Therefore, from the result of the above cyt C release from the core-shell structured scaffolds, it can be further confirmed that designing scaffolds that can deliver dual growth factors that are different from each other is feasible by placing the rapid releasing factor at the shell part and the one that requires a more sustainable release profile at the core part.

Also, the present invention provides core-shell structured fibrous scaffolds that were prepared by the above method.

The present invention discloses concentric fibrous scaffolds having a core-shell structure, and can provide scaffolds that can release 2 types of growth factors in time-dependent sequential mode by respectively incorporating the 2 types of growth factors to the core part and shell part.

In one Example of the present invention, a composition that has alginate (Alg) with α-tricalciumphosphate (α-TCP) added in various amounts has been used. Self hardening of scaffolds was feasible by crosslinking Alg within the $CaCl_2$ solution during the deposition process. The scaffold form was preserved at this point and the incorporated growth factor was protected. The Alg used by scaffolds for delivering the growth factor was a biocompatible hydrogel that provides a favorable microenvironment condition for cells. Alg has a feature of being sensitive to external stimulation and useful in the delivery of drugs. Also, usage of α-TCP enhanced the feature of scaffolds in ways that are particularly helpful for the functions of the bone associated cells. The setting property has been confirmed to positively affect the stability and rigidity of the scaffolds.

Based on the above result, in one Example of the present invention, Alg-based scaffolds structured to be core-shell fibrous by coaxial depositing within the $CaCl_2$ solution have been designed and model protein has been used to study the feasibility of realizing the above scaffolds which can effectively load and deliver the growth factor. As a result, the scaffolds of the present invention have been confirmed to be capable of being used in a scaffold system that can deliver dual growth factors.

The core-shell structured fibrous scaffold system of the present invention has been designed by the direct deposition of Alg/α-TCP and in situ hardening to load and deliver proteins. During the Alg crosslinking, a release of protein initially loaded was inevitable, and shortening the crosslinking time was effective in reducing protein release. From Alg scaffold, the cyt C, used as the model protein, was released rather rapidly initially (within a day) and then reached a plateau. However, the α-TCP addition (up to 75%) significantly improved the sustainable and continual release of cyt C for up to 6 weeks, suggesting better performance of delivering growth factors. Appropriate core-shell designs to deliver dual growth factors could be proposed based on the results, by positioning the rapid-releasing factor at the outer shell and the slow-releasing factor at the inner core part. Varying compositions of each part with different α-TCP additions can extend the variability of release profiles. Therefore, it was confirmed that the core-shell-structured rapid hardening Alg/α-TCP scaffolds of the present invention are effective to loading and delivering of growth factors.

Advantageous Effects

The present invention, by adding calcium phosphate cement and a protein, drug or combination thereof to the alginate solution and preparing a core part composition and shell part composition that each have a different composition, and then inserting the above core part composition and shell part composition to inner and outer-nozzles, respectively, subsequently injecting the core part composition and shell part composition to the calcium ion aqueous solution to be hardened, has the effect of preparing core-shell structured rapid hardening Alg/α-TCP scaffolds that can controllably release a protein or drug.

BEST MODE

Figure 1:
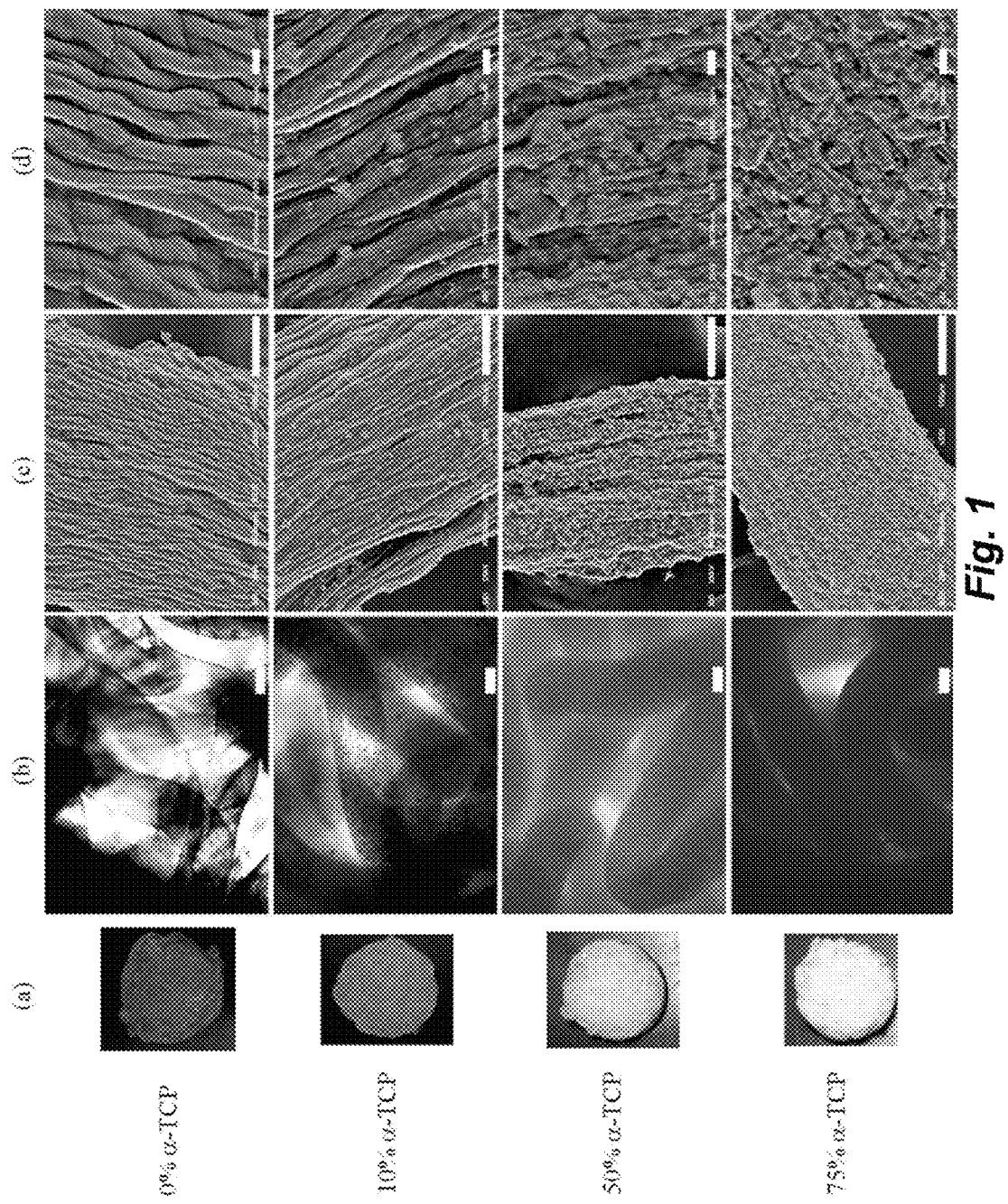
FIG. 1 shows the structure of Alg and Alg/α-TCP scaffolds obtained by dispensing and hardening in the $CaCl_2$ solution observed with a naked eye (a), optical microscope image (b) (scale bar: 300 μm), low magnification SEM image (c) (scale bar: 100 μm) and high magnification SEM image (d) (scale bar: 10 μm).

The present invention is explained in more detailed through the Examples below. However, these Examples are merely intended to illustrate the present, invention and are not intended to limit the scope of protection.

Example 1 Materials and Methods

Materials and Fibrous Scaffold Deposition

α-TCP was obtained by sintering a mixture of calcium hydrogen phosphate ($CaHPO_4$, Sigma-Aldrich, C7263) and calcium carbonate ($CaCO_3$, Sigma-Aldrich, 239216) at 1400° C. and subsequent quenching. The sintered powder was milled in a planetary mill and added with 2 wt % hydroxyapatite (HA) crystallites as a seed for the phase-trans format, ion of cement from α-TCP into HA. The α-TCP had a median particle size of 5.2 μm as determined from laser diffraction (Malvern, APA5001SR).

Na-Alg (Sigma-Aldrich, A2158) was dissolved in water at two different, concentrations (3 or 5%). The α-TCP powder was mixed with the Alg solution at ratios of 10, 50, or 75 wt % of α-TCP with respect to the composite. For the scaffolding process, a dispensing machine (KD Scientific) was used. The mixture was dispensed into a fiber form through a 23G syringe at an injection rate of 50 mL/h into a bath containing $CaCl_2$ (150 mM or 1 M in distilled water), during which the fibrous scaffold form was preserved without being disintegrated by the crosslinking reaction of Alg with calcium ions. After dispensing 0.5 mL of the solution, the dispensed scaffolds were left in the $CaCl_2$ solution for different times to better conduct crosslinking (crosslinking time: 1, 5, 10, and 30 min). Afterward, the fibers were shaped in a Teflon mould with dimensions of 12 mm diameter×6 mm height.

Design of Core-Shell Scaffolds

A concentric nozzle (inner 17G and outer 23G) was specifically designed and used to produce core-shell-structured fibrous scaffolds. Each solution with specific composition (Alg or Alg/α-TCP) as described in the below Table 1 was separately fed into the outer and inner syringes. The compositions of the core-shell were varied as summarized in Table I. Each syringe was attached to an injection pump connected through a microtube. Core-shell-structured Alg fiber was then injected at a rate of 50 mL/h through the coconcentric nozzle within a bath containing 150 mM $CaCl_2$ solution for 1 min.

TABLE 1

| Case in which protein[1] is comprises in the shell part[2] | | Case in which protein[1] is comprised in the core part[2] | |
|---|---|---|---|
| α-TCP content of Core part (wt %) | α-TCP content of Shell part (wt %) | α-TCP content of Core part (wt %) | α-TCP content of Shell part (wt %) |
| 0 | 0 | 0 | 0 |
| 0 | 10 | 0 | 10 |
|  |  | 50 | 0 |

[Note]
[1] cytochrome C(cyt C)was used as model protein
[2] protein is designed to be comprised in either the shell part or the core part Characterization and Mechanical Tests Scanning electron microscopy (SEM) was carried out using a JEOL JSM-6510 apparatus to investigate the microstructure of the scaffolds. The samples were sputtered with platinum for the SEM examination. The mechanical properties of the scaffolds (12 mm diameter×6 mm height) were measured by dynamic mechanical analysis (DMA; MetraVib, DMA25N) in the parallel plate configuration. Mechanical spectrometry was carried out using dynamic frequency sweep with frequencies ranging from 0.1 to 10 Hz at 37° C. and with strain amplitude of 5%, which was in the linear region of viscoelasticity. Both autotension and autostrain adjustments were applied. Force was ramped from 0.001 to 0.2 N, and the maximum allowed strain was set at 10%. The storage modulus and loss modulus (E") of the samples were measured.

Protein Loading and Release from the Scaffolds

First, the capacity to in situ load proteins within the fibrous scaffolds during the dispensing process was observed.

Cytochrome C (cyt C) was used as the model protein, reflecting its common use as the model for growth factors. 500 μg of cyt C was added to 0.5 mL of solution (either Alg or Alg/α-TCP composites), which was then dispensed into fibrous scaffolds in $CaCl_2$ solution. For the case of core-shell scaffolds, cyt C loading was designed to be within only the inner or outer part, and the effect of the compositional change (inner or outer composition) on the release of protein was investigated. After crosslinking the scaffolds for different time points (1, 5, 10, and 30 min), the amount of cyt C was analyzed from the supernatant to detect the loading quantity. The amount of cyt C released was measured using a Libra S22 spectrophotometer at an absorbance 408 nm (Biochrom). Loading experiments continued by changing other crosslinking parameters, including concentration of Alg (3 and 5%) and $CaCl_2$ (150 mM and 1 M). Furthermore, the effect of α-TCP amount in the mixture solution with Alg (0-75 wt % of α-TCP) was also investigated. To study the release of cyt. C from the scaffolds, each scaffold sample was immersed in 1 mL phosphate buffered saline (PBS) for different periods of up to 42 days. The cyt C released was assessed spectrophotometrically at an absorbance of 408 nm using the aforementioned Libra S22 apparatus. The release quantity was interpreted after normalized to the loaded quantity. The medium was refreshed at each time point of the assay.

Example 2 Characteristics of Deposited Fibrous Scaffolds

The macroscopic morphology of the Alg and Alg/α-TCP scaffolds obtained by means of dispensing and hardening in $CaCl_2$ solution is shown in FIG. 1. The addition of α-TCP powders rendered the scaffold opaque. An extensive fibrous network with highly macroporous structure developed for all scaffolds, which was expected to allow cell migration and penetration (Lee G S et al., Acta Biomater, 2011, 7, 3178-3186). Optical images of the composite scaffolds revealed the dispersion of α-TCP particles (several micrometers in size) in the Alg matrix. The sizes of the fibers and the interspacings (macropores) of the scaffolds with different compositions were similarly observed; fibers of ~200-250 μm and macropores of ~200-500 μm. SEM images also revealed α-TCP particles distributed in the Alg phase. When the amount of α-TCP was high (75%), the Alg fibers were completely covered with α-TCP. A similar morphological feature has also been observed in the collagen/α-TCP scaffold (Perez R et al., J Mater Sci Mater Med, 2011, 22, 887-897). It should be borne in mind that α-TCP transforms to calcium-deficient HA under physiological conditions, leading to phases consisting of Alg and HA (Lee G S et al., Acta Biomater, 2011, 7, 3178-3186; Perez R et al., J Mater Sci Mater Med, 2011, 22, 387-897). As the α-TCP-containing composites retain the biomimetic carbonated apatite phase, they are considered to provide beneficial matrix conditions in terms of chemical composition for cells to engage in osteogenesis and to function in bone formation.

Figure 2:
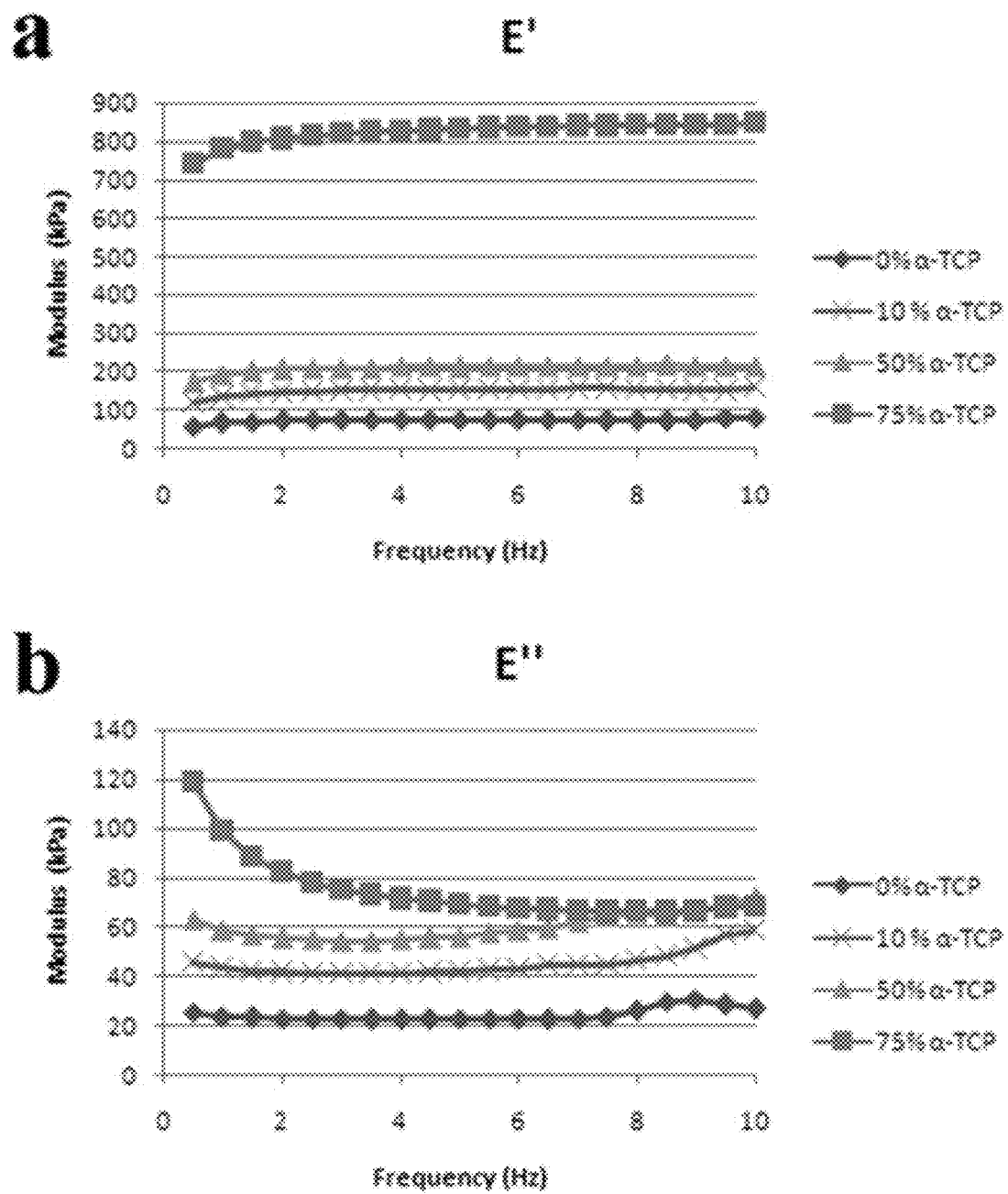
FIG. 2 is a DMA result of alginate-based fibrous scaffolds according to different α-TCP content, and the change in storage modulus (E') (a) and loss modulus (E") (b) value according to the frequency (0.1-10 Hz), shown as graph.

The effect of the α-TCP incorporation (10, 50, and 75%) into scaffolds on the mechanical properties was investigated under dynamic conditions using DMA. Storage modulus (E') and loss modulus (E') values were recorded as a function of frequency (0.1-10 Hz) as shown in FIG. 2. For all cases, the E' values were higher than the E" values, demonstrating that the fibrous scaffolds behaved in a more elastic fashion than as a viscous network. The higher the amount of α-TCP added, the higher were the mechanical properties (both E' and E"), with the E' change being especially pronounced, suggesting the stiffening role of α-TCP phase in the polymeric Alg. The E' values of the Alg/α-TCP composite scaffolds were about 150, 200, and 800 kPa with 10, 50, and 75% α-TCP addition, respectively, which were significantly enhanced values with respect to that of Alg scaffold (~80 kPa). The stiffness of the scaffolds could be tuned with the addition of α-TCP. It is worth noting that for the case of 75% α-TCP/Alg composite scaffold, the improvement was as high as ~10 times.

Example 3 Loading of Cyt C and Crosslinking of Scaffolds

Having confirmed the beneficial properties of the Alg/α-TCP composite scaffolds in the above Example 2, it was investigated the capacity of the scaffolds in loading and delivering therapeutic molecules, particularly growth factors.

Cyt C was used as the model protein. It has been frequently used to represent the behavior of growth factors like fibroblast growth factors owing to the similarity in size and charge characteristic. First, it was observed the loading behavior of cyt C within the scaffolds. Cyt C was loaded in situ within the material solution, which was then allowed to harden in highly concentrated $CaCl_2$ solution due to the effective crosslinking of Alg phase and scaffold. Thus, it was possible that the crosslinking step influences the loading behavior of cyt C. In fact, a preliminary study established that a large portion of cyt C initially used was released during the crosslinking process. Therefore, in this example, it was analyzed systematically the loading behavior of cyt C in the crosslinking step by varying the crosslinking conditions, such as $CaCl_2$ concentration (150 mM or 1 M), Alg concentration (3 or 5%), and crosslinking time (1, 5, 10, and 30 min). The effect of divalent ions on the Alg crosslinking has been previously studied. $Ca^{2+}$ produced better performance than other cations including $Ba^{2+}$ and $Sr^{2+}$ (Acarturk S T, J. Microencapsul., 1999, 16, 275-290). The $Ca^{2+}$ ions replace $Na^+$ ions in Alg structure and make strong bonds with Alg through ionic interactions, forming a crosslinked network. Therefore, it was considered that the ion concentration and Alg concentration (3 and 5%) should importantly determine the crosslinking process and the resultant Alg-Ca networks. Increasing the $Ca^{2+}$ ions-would be helpful for more crosslinks, whereas certain optimal Alg concentrations may exist to achieve rapid crosslinking as well as more highly crosslinked structure. Moreover, a certain time period may be required to complete crosslinks.

Figure 3:
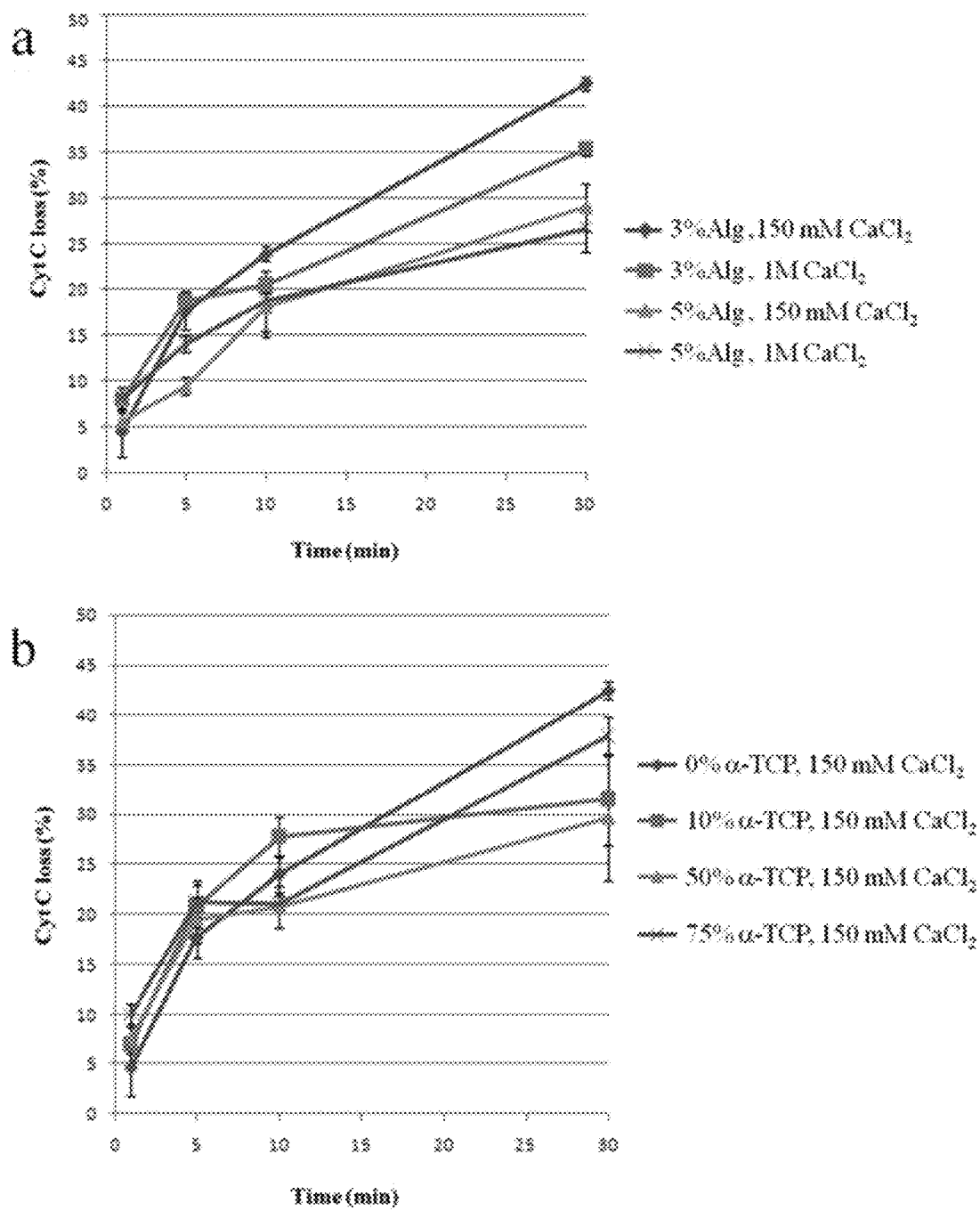
FIG. 3 shows in graph the release amount of cyt C released from scaffolds during process of crosslinking in various crosslinking conditions, (a) represents the release amount of cyt C due to change in alginate (Alg) and $CaCl_2$ concentration while using pure alginate (Alg) aqueous solution, and (b) represents release amount, of cyt C due to change in α-TCP content.

The release quantity of cyt C released from the scaffolds during the crosslinking process at varying crosslinking conditions is shown in FIG. 3(a). Alg scaffold was used for this study. It was clear that the crosslinking time affected the cyt. C release most significantly although there were some differences in the cyt C release depending on the other parameters (Alg or $CaCl_2$ concentration). Cyt C release continued to increase with increasing time. Specifically, 5-7% at 1 min became ~22-43% at 30 min.

The effect of α-TCP addition on the cyt C release was also investigated (FIG. 3(b)). A similar cyt C release behavior was observed in all the α-TCP-added composite scaffolds, with no clear effect of the amount of α-TCP: an on-going cyt C release with crosslinking time. Therefore, it is concluded that the release of cyt C protein is primarily dependent on the crosslinking time. Thus, shortening the crosslinking time is inevitable to reduce the protein release.

Figure 4:
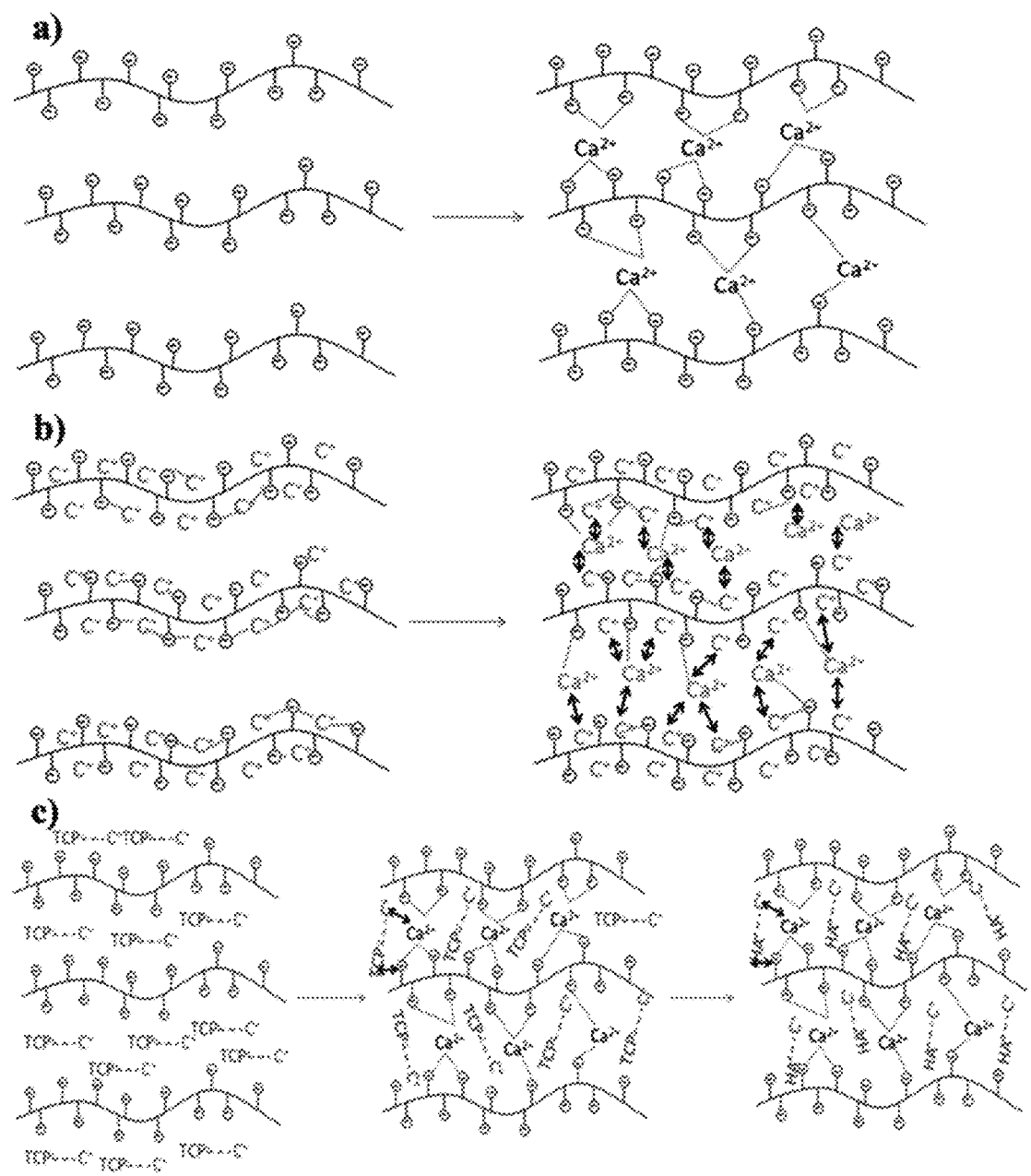
FIG. 4 shows a feasible mechanism for the initial release of cyt C from Alg-based scaffolds.

The possible mechanism of the initial release of cyt C from the Alg-based scaffolds is illustrated in FIG. 4. Compared to crosslinking of pure Alg [FIG. 4(a)], when cyt C protein was pooled in the Alg solution [FIG. 4 (b)], it can bind to Alg molecules through weak interactions as cyt C has a net positive charge, whereas Alg is negatively charged. However, when immersed in $CaCl_2$ solution, $Ca^{2+}$ ions bind Alg molecules more strongly, repelling cyt C molecules, which results in initial cyt C release. When α-TCP powders are added to Alg solution [FIG. 4(c)], there should also be interactions of cyt C with α-TCP, which however, also are not enough to overcome the ion exchange by $Ca^{2+}$ and cyt C release out from the scaffolds during the crosslinking process. Storing the scaffolds in a highly concentrated $CaCl_2$ cross linking solution will cause high influx of Ca ions, which drives the release of cyt C molecules from the scaffolds. It is also considered that the cyt C molecules pooled in the Alg/α-TCP solution could not have sufficient time to be tightly adsorbed on the surface of α-TCP particles. Therefore, the weakly bound cyt C molecules, particularly those present at the outer surface of the fibers, should be released rather rapidly at the beginning stage of crosslinking. Thus, combining cyt C with α-TCP powders could initially possibly help lessen the rapid cyt C release. Moreover, it should also be noted that the α-TCP state transforms to an apatite state with time, which will affect the release of cyt C molecules at a much later stage [FIG. 4 (c)].

Example 4 Prolonged Release of Cyt C from the Scaffolds

Figure 5A:
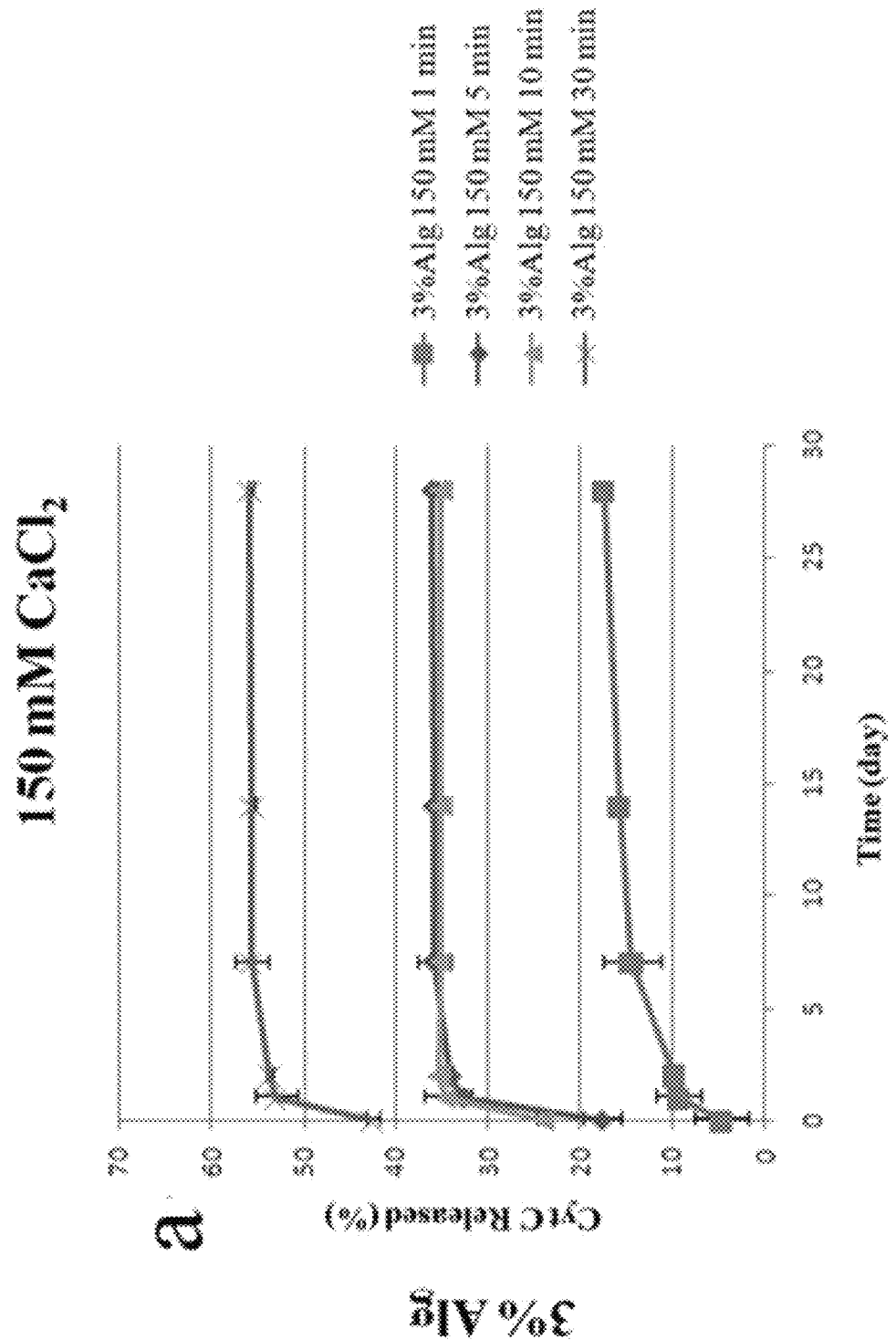
FIG. 5 is a result of studying the release of cyt C from the fibrous scaffolds up to day 28. (a) represents a case when Alg scaffolds are prepared using 3% Alg and 150 mM $CaCl_2$ solution, (b) represents a case when Alq scaffolds are prepared using 3% Alg and 1 M $CaCl_2$ solution, (c) represents a case when Alg scaffolds are prepared using 5% Alg and 150 mM $CaCl_2$ solution, (d) represents a case when Alg scaffolds are prepared using 5% Alg and 1 M $CaCl_2$ solution.
Figure 5B:
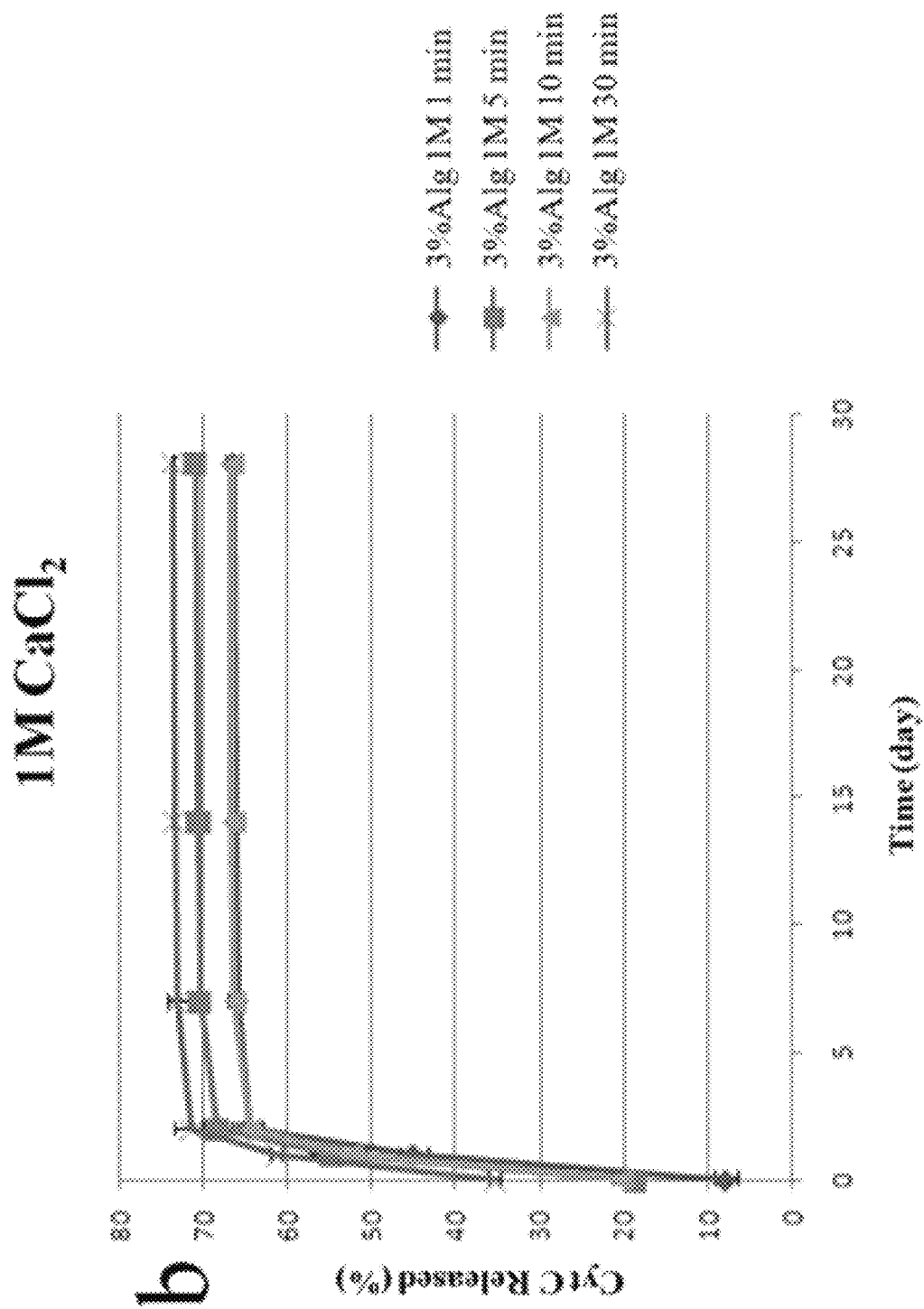
Figure 5C:
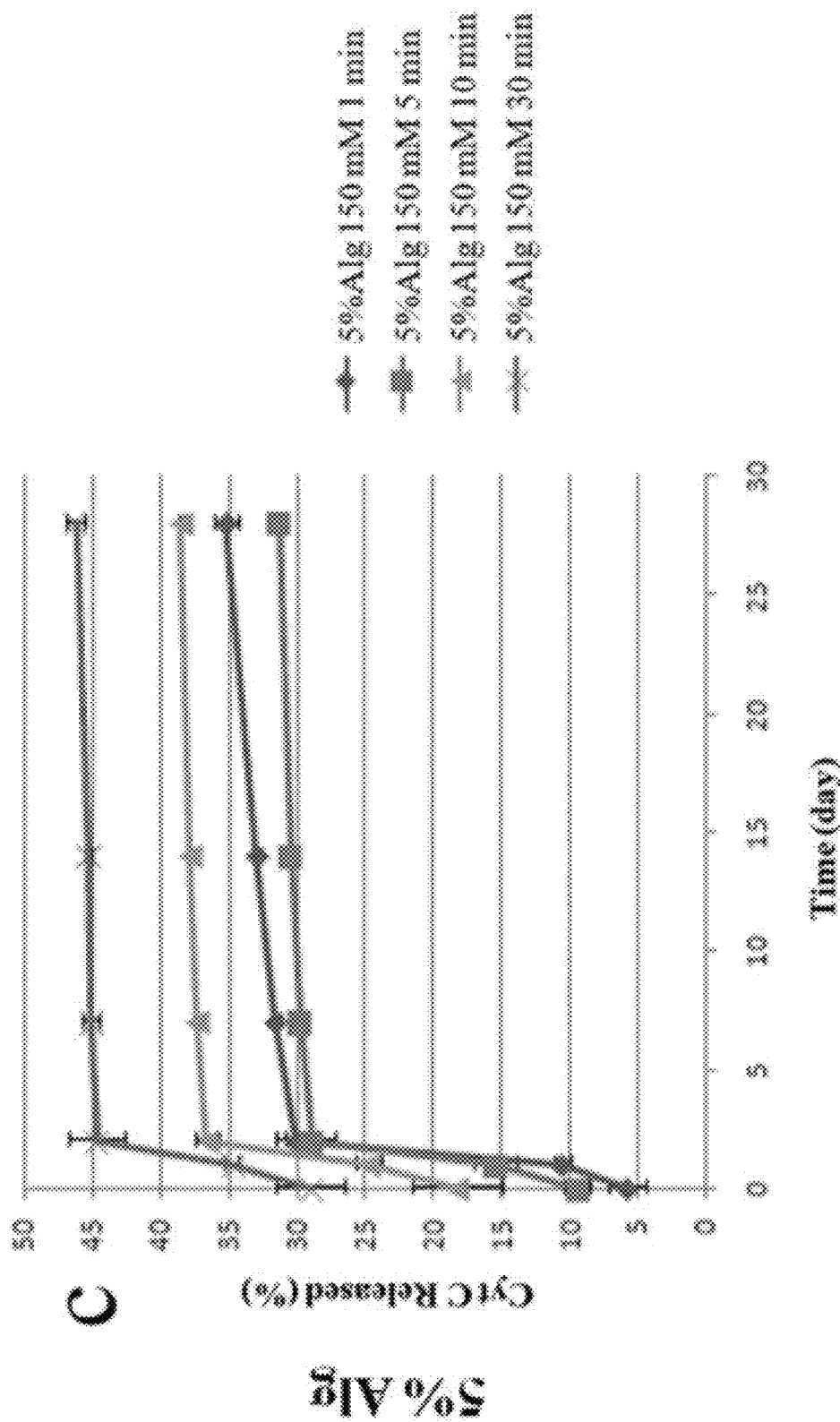
Figure 5D:
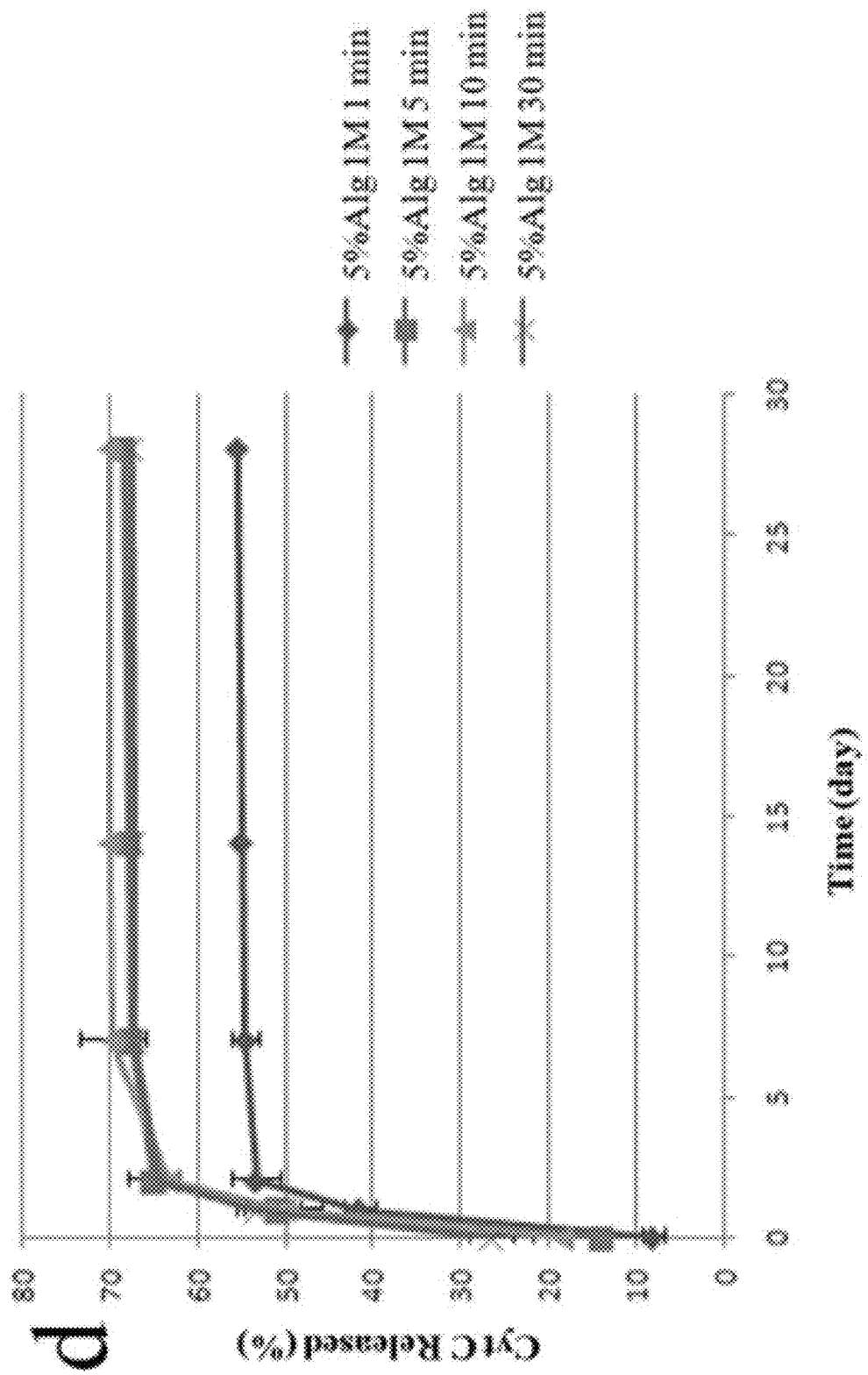

The release of cyt C from the fibrous scaffolds was examined in PBS at 37° C. for periods up to 28 days. Tests were made at different cross-linking conditions and results were plotted considering the cyt C release amount, as the starting point of each graph (FIG. 5). For the Alg scaffolds prepared with 3% Alg and under 150 mM $CaCl_2$ solution [FIG. 5(a)], crosslinking times over 5 min resulted in high initial burst. (~15% for 1 day) and almost, saturation in the release, however, a short crosslinking time of 1 min showed a slow and steady release of cyt C over the period of 28 days although the total release amount was ~18%. In the case of higher Alg concentration (5%), the scaffolds prepared at both $CaCl_2$ concentrations showed the initial burst effect and a saturation behavior without regard to the crosslinking time (FIG. 5c and FIG. 5d). Based on the results, the crosslinking of 3% Alg in 150 mM $CaCl_2$ for 1 min showed only the possible sustainable and continual release profile of cyt C, which however, exhibited a very limited amount of cyt C released (~18%), even after 28 days.

Figure 6:
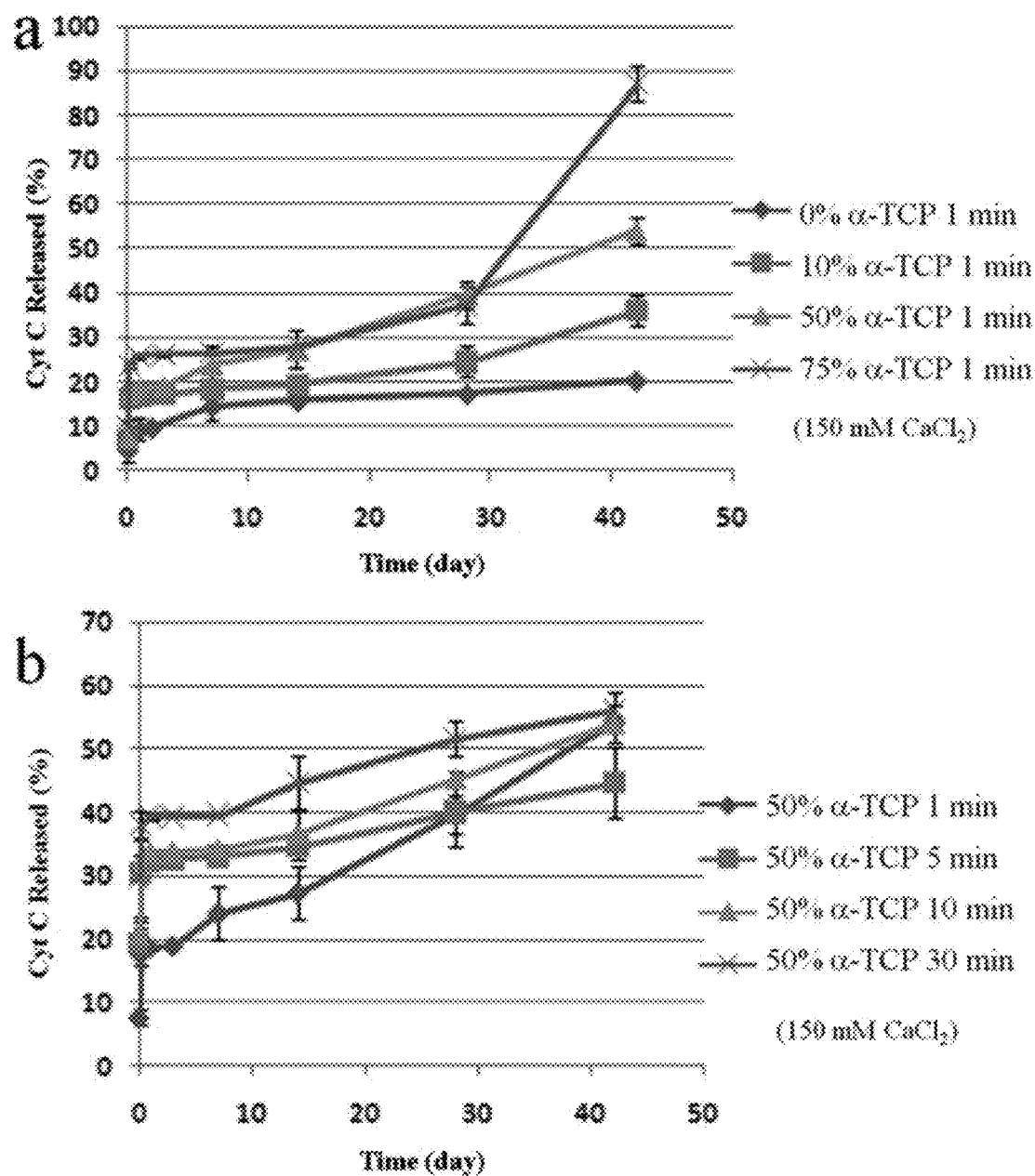
FIG. 6 is a graph showing release behavior of cyt C when α-TCP is added to the Alg scaffolds, (a) represents a case when the scaffolds have different α-TCP content, and was prepared through 1 min of crosslinking time, and (b) represents a case when the scaffolds have 50 wt % of α-TCP, and were crosslinked under varying time.

The effects of α-TCP addition to the Alg scaffolds on the cyt C release behaviors were also observed as shown in FIG. 6. The composite scaffolds crosslinked for the short time of 1 minute [FIG. 6(a)] profiled a continual release of cyt C, and the addition of α-TCP significantly enhanced the release rate with time. Consequently, after 42 days (6 weeks), the total release amounts were ~35, 48, and 80% for 10, 50, and 75 wt % α-TCP, respectively (higher than ~18% for pure α-TCP), given that the cyt C release amount was small and almost similar (~5-7%). The 50% α-TCP/Alg scaffolds obtained with different crosslinking time exhibited similar on-going release profile with time, without showing a plateau, being different from those observed in pure Alg [FIG. 6(b)], In consideration of the initial cyt C release amounts of each case (higher release corresponding with longer crosslinking time), the consequent cyt C release amounts were ~48% (1 min), ~25% (5 min), ~35% (10 min), and ~25% (30 min), demonstrating different release amounts with respect to crosslinking time. Taking all the release profiles of cyt C from the α-TCP-added Alg scaffolds into account, the noteworthy finding was the continual (much like zero-order) and sustainable (still releasing after 6 weeks) release profiles without regard to the crosslinking time (and, thus, initial cyt C release), which contrasted to the cases observed in pure Alg scaffolds. These facts support the potential usefulness of the α-TCP/Alg composite scaffolds for continual long-term delivery of growth factors. Furthermore, the big difference in the release rate of the scaffolds achieved by varying the α-TCP amount should be properly utilized in applying the system for delivery of growth factors at a controllable rate and quantity. Thus, the core-shell-structured scaffolds were designed to have the position of the composition of the core or shell part adjusted, to thereby incorporate growth factors separately and tailor their sequential release.

Example 5 Core-Shell Structured Scaffolds and Cyt C Release

Figure 7:
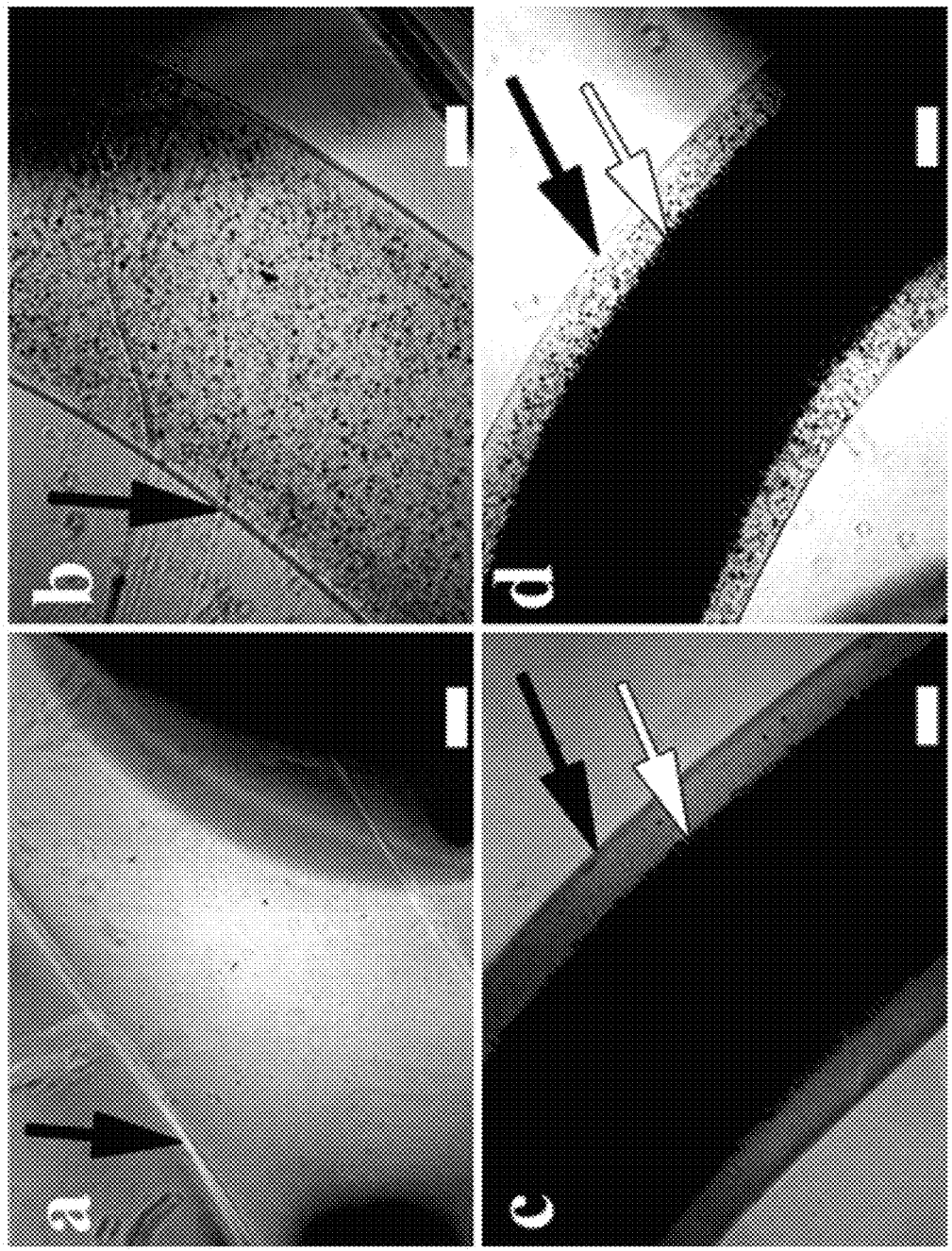
FIG. 7 is an optical image of core-shell structured fibrous scaffolds prepared through usage of concentric nozzle. (a) represents a case wherein the core part consisted of pure Alg core part and the shell part consisted of pure Alg, (b) represents a case wherein the core part consisted of Alg and the shell part, consisted of 10 weight % α-TCP, (c) represents a case wherein the core part consisted of 50 weight % α-TCP and the shell part consisted of pure Alg, and (d) represents a case wherein the core part consisted of 50 weight % α-TCP and the shell part consisted of 10 weight % α-TCP.

FIG. 7 shows the optical image of the core-shell-structured fibrous scaffolds produced by using a concentric nozzle. Different compositions were used to comprise the core and shell parts. Owing to the differing amounts of α-TCP powders added to the scaffold, the core-shell structure was optically discernible. As the same injection speed was used for both core and shell, the volume of core and shell was equal, and the measurement of volume from the two-dimensional images (core diameter of ~1400 μm and shell thickness of ~300 μm, and taking cylindrical shape) also gave a similar result.

Figure 8A:
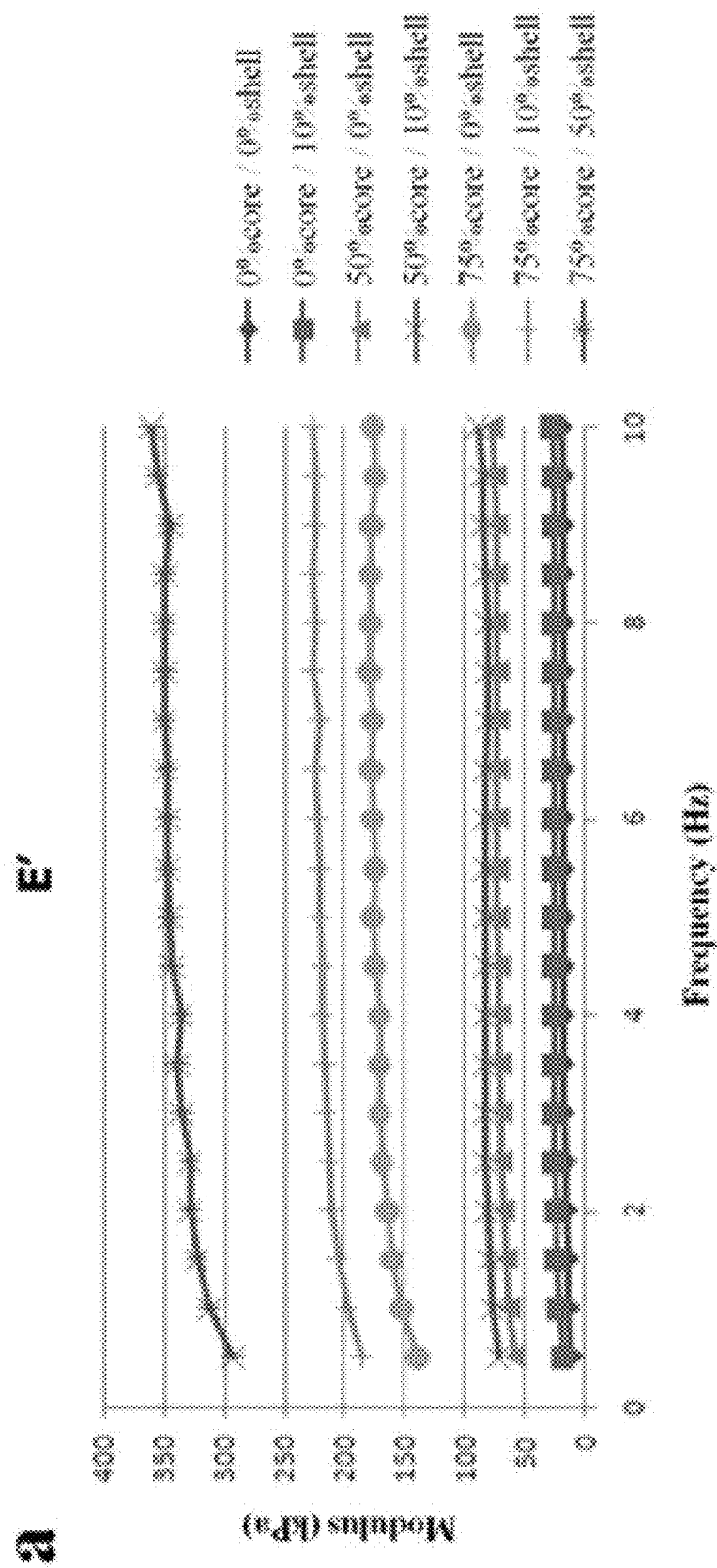
FIG. 8 is the DMA result of core-shell scaffolds with other compositions, showing in graph the change in storage modulus (E') (a) and loss modulus (E") (b) value according to frequency (0.1-10 Hz).
Figure 8B:
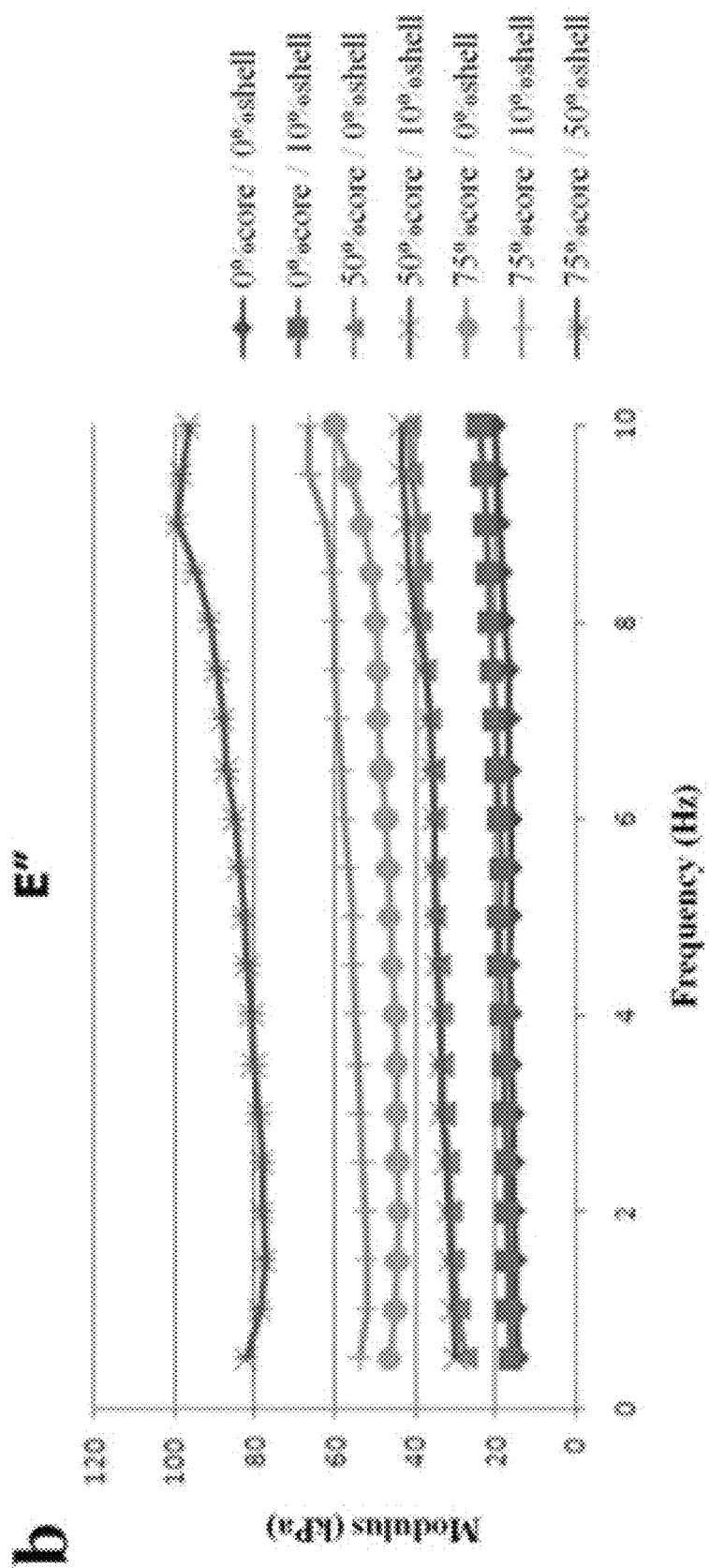

The DMA of the core-shell scaffolds with different compositions was also performed as shown in FIG. 8. The Alg of the core-shell-structure showed storage modulus (E'~10-20 kPa and loss modulus (E") ~15-20 kPa, which were smaller than the values in single Alg fiber (vs. FIG. 2), and this may be due to the difference in whole fiber size (~650 μm for single fiber vs. ~2000 μm for dual fiber) and the consequent macroporosity between fibers. The addition of α-TCP either to core or to shell increased both modulus values and the more so in E' values, suggesting a more significant role in elastic stiffening of the Alg-based scaffolds. This improvement in modulus values with α-TCP addition was similarly observed in single fibers. As a whole, the modulus values were higher in the scaffold when the total amount of α-TCP present in the core and shell part was higher: 0%<10% shell<50% core<50% core+10% shell<75% core<75% core+10% shell<75% core+50% shell. Again, the mechanical stiffness values, largely mimicking native bone, of the α-TCP-added scaffolds with core-shell structure in comparison to the Alg scaffolds, are of great merit for their use in bone tissue engineering applications.

Further, the cyt C release behavior from the core-shell-structured scaffolds was investigated. Cyt C was loaded in either the shell or the core part while varying the composition of each part. It was thought that the cyt C loaded in the core would show a delayed release profile owing to the outer shell layer, being compared to the case loaded in the shell, which would release more quickly. Moreover, varying the composition (α-TCP/Alg amount) of either core or shell will alter the cyt C release profile.

Figure 9:
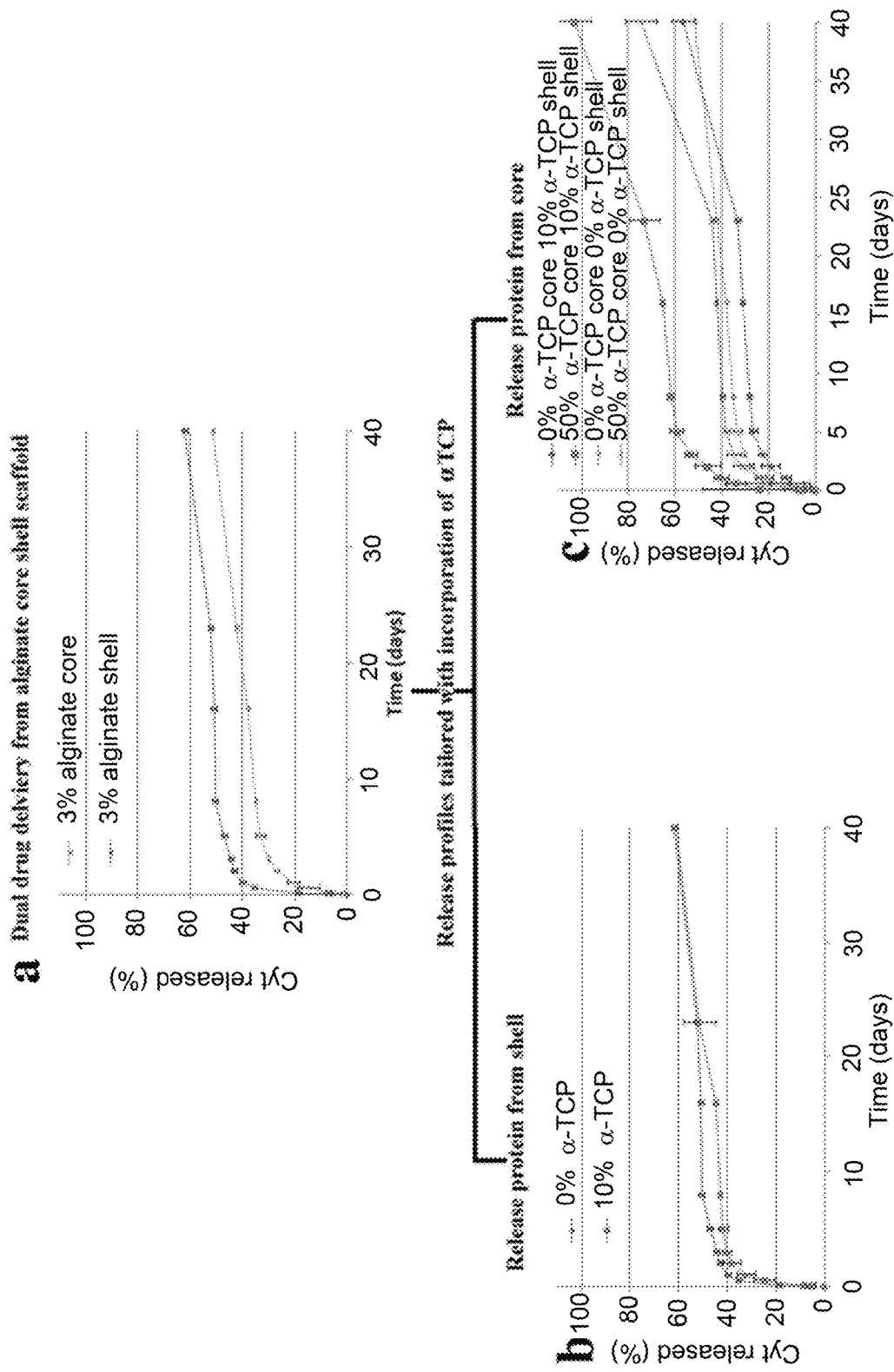
FIG. 9a is a graph showing the result acquired from observing the release behavior after using Alg core-shell scaffolds and loading cyt C into any one of core part or shell part.
FIG. 9b is a graph showing the result acquired from observing the cyt C release after changing the composition of any one of the core part or shell part while changing the amount of α-TCP.
FIG. 9c is a graph showing the result acquired from observing the cyt C release after changing the composition of any one of the shell part or core part when cyt C is loaded into the core part.

First, with Alg core-shell scaffold [FIG. 9(a)], cyt C was loaded in either core or shell part, and the release behavior was observed. As expected, the cyt C release from the core showed a delayed pattern with respect, to that released from the shell. Results demonstrated clearly that by switching the loading of cyt C in either core or shell it was possible to control the release profile of cyt C.

Next, the composition of either the core or the shell was changed by varying the α-TCP amount and then the cyt C release was observed. When cyt C was loaded into the shell [FIG. 9(b)], the compositional variation (Alg vs. 10% α-TCP) showed different release profiles: lower initial burst and an on-going release profile with TCP addition, as was similarly observed in the case of single fiber scaffolds (FIG. 6).

When cyt. C was loaded in the core [FIG. 9(c)], changing the composition of either shell or core part also affected the protein release. At the core composition of pure Alg, cyt C release from the core only slightly changed depending on the shell composition (FIG. 9c green line (-▲-) vs blue line (-♦-). When the core composition was 50% α-TCP/Aig, the cyt. C release from the core was substantially enhanced with respect to the cases with Alg in the core (FIG. 9c, red line (-■-) and purple line (-×-)). Furthermore, the release was significantly higher when the core part, composition was 50% α-TCP/Alg then when shell part contained 10% α-TCP (FIG. 9c purple line (-×-) vs red line (-■-). In particular, for this case, the total cyt C release amounts at 42 days were as high as 80-100%, and continual releases were achieved 5 days onward.

The results of cyt C release from the core-shell-structured scaffolds support the design of a scaffold that can carry dual growth factors, where the rapid releasing factor is placed at the shell part while the one requiring more sustainable profile at the core part. This is easily implementable just by positioning each factor at different parts during the deposition process, and is primarily the benefit of the crosslinking nature of the Alg scaffold in divalent ionic solution. Although the process is conducted under water-based (non-toxic solvent) and mild temperature conditions, the high ionic concentration required to crosslink Alg resulted in some release (leaching out) of proteins. A possible way to preserve a major amount of proteins was to shorten the crosslinking time (i.e., by several minutes), and this was a universal phenomenon without regard to the scaffold compositions. As to the effects of α-TCP, it can be envisaged that tuning the release rate can be more ambitious when the α-TCP was introduced into Alg scaffold. Adding the α-TCP up to 75% enabled the scaffolds to release cyt C continuously at relatively high quantity for a long period (over 6 weeks), which potentiates the capacity of the dual-structured α-TCP/Alg composite scaffolds in loading and longterm delivery of growth factors.

Using specific growth factors targeting bone regeneration, such as osteogenic factors (e.g., BMPs) and angiogenic factors (e.g., VEGF) to position each part of the core-shell structure with proper compositions, is one example. The loading of VEGF in the shell while positioning BMP in the core part of Alg will get the profile of sequentially released VEGF and BMP, for all the compositions chosen as deduced from FIG. 9(a). Furthermore, altering the composition of each part also controls the sequential release rate of the two different growth factors. Specifically, using 0% α-TCP sustains more the release of BMP placed in the core than using 10% α-TCP as deduced from FIG. 9(c).

The invention claimed is:

1. A method for preparation of a core-shell structured fibrous scaffolds capable of releasing a first protein, drug or combination thereof and a second protein, drug or combination thereof different from the first protein, drug or combination thereof, comprising the following steps:

adding calcium phosphate cement, and the second protein, drug or combination thereof to alginate solution to prepare a core part composition;

adding calcium phosphate cement, and the first protein, drug or combination thereof to alginate solution to prepare a shell part composition; and inserting the core part composition and shell part composition into an inner and outer nozzle of a concentric nozzle respectively;

extruding the resultant core part composition and the resultant shell part composition into a calcium ion aqueous solution so as to form the fibrous scaffolds, in which alginate is cross-linked simultaneously with the hardening of calcium phosphate cement, wherein the alginate solution has a concentration of 1 to 10 weight %; the amount of the calcium phosphate cement in the core part is 10 to 75 weight %, and the amount of the calcium phosphate cement in the shell part is 10 to 75 weight %;

the amount of the calcium phosphate cement in the core part is different from the amount of the calcium phosphate cement in the shell part to control release speed of the protein, drug or combination thereof differently; and the calcium phosphate cement consists of an aqueous solution comprising phosphate particles and a substance which catalyzes hardening of the cement, wherein the substance which catalyzes hardening of the cement is hydroxyapatite (HA).

2. The method according to claim 1, in which the calcium phosphate is tricalcium phosphate, monocalcium phosphate, tetracalcium phosphate, dicalcium phosphate, or a combination thereof.

3. The method according to claim 1, in which the protein is growth factor, bovine serum albumin, lysozyme or a combination thereof.

4. The method according to claim 3, in which the growth factor is bone formation factor, angiogenesis factor, or a combination thereof.

5. The method according to claim 1, in which the above drug is antibiotics, an anticancer drug, anti-inflammatory drug or a combination thereof.

6. The method according to claim 1, in which the concentration of the calcium ion is 10 mM to 3 M.

7. The method according to claim 1, in which a hardening time of the calcium phosphate cement is 1 to 10 minutes.

8. A core-shell structured fibrous scaffold which is prepared by the method of claim 1.

* * * * *